(12) United States Patent
Li et al.

(10) Patent No.: US 6,372,958 B1
(45) Date of Patent: Apr. 16, 2002

(54) TRANSGENIC MOUSE WITH ENDOGENOUS ENDOGLIN GENE DISRUPTION

(75) Inventors: Dean Y. Li; Mark T. Keating, both of Salt Lake City, UT (US)

(73) Assignee: The University of Utah Research Foundation, Salt Lake City, UT (US)

(*) Notice: Subject to any disclaimer, the term of this patent is extended or adjusted under 35 U.S.C. 154(b) by 0 days.

(21) Appl. No.: 09/578,553

(22) Filed: May 25, 2000

Related U.S. Application Data

(60) Provisional application No. 60/136,089, filed on May 26, 1999.

(51) Int. Cl.[7] .................. A01K 67/027; A01K 67/00; C12N 15/00; C12P 21/00; G01N 33/00
(52) U.S. Cl. .................. 800/18; 800/3; 800/22; 800/8; 800/9; 800/21
(58) Field of Search .................. 800/3, 8, 9, 18, 800/22, 21; 435/354

(56) References Cited

U.S. PATENT DOCUMENTS 6,022,687 A * 2/2000 Letarte et al. .................. 435/6

OTHER PUBLICATIONS

Bourdeau, et al., 1999. Journal of Clinical Investigation, vol. 104, No. 10, pp. 1343–1351.*
Moreadith, et al., 1997. J. Mol. Med., vol. 75, pp. 208–216.*
Fassler et al., Knockout mice: How to make them and why. The immunological approach, 1995, Int Arch Allergy Immunol. vol. 106, pp. 323–334.*
Balconi, Giovanna et al., "Development of Endothelial Cell Lines From Embryonic Stem Cells," Arterioscler Thromb Vasc Biol., Jun., 2000, vol. 20, p. 1443–1451.
Bourdeau, Annie, et al., "A Murine Model of Hereditary Hemorrhagic Telangiectasia", The Journal of Clinical Investigation, Nov., 1999, vol. 104, No. 10, p. 1343–1351.
Bonyadi, Mortaza, et al., "Mapping of a major genetic modifier of embryonic lethality in TGFβ1 knockout mice.", Nature Genetics vol. 15, Feb., 1997, p. 207–211.
Dickson, Marion C., et al., "Defective Haematopoiesis and Vasculogenesis in Transforming Growth Factorβ1 knock out mice.", Development, 1995, vol. 121, p. 1845–54.

Glick, Adam, B., et al., "Loss of Expression of Transforming Growth Factor β in Skin and Skin Tumors is Associated with Hyperproliferation and a High Risk for Malignant Conversion.", Proc. Natl. Acad. Sci. USA, vol. 90, pp. 6076–6080, Jul., 1993.
Gualandris, Anna, et al., "The Latent Transforming Growth Factor–β–binding Protein–1 Promotes In Vitro Differentiation of Embryonic Stem Cells Into Endothelium.", Molecular Biology of the Cell., Dec. 2000, vol. 11, p. 4295–4308.
Hatzopoulous, Antonis K., et al., "Isolation and Characterization of Endothelial Progenitor Cells From Mouse Embryos," Development 125, 1998, p. 1457–1468.
Li, Dean Y., et al., "Elastin Point Mutations Cause An Obstructive Vascular Disease, Supravalvular Aortic Stenosis," Human Molecular Genetic, 1997, vol. 6, No. 7, p. 1021–1028.
Li, Dean Y., et al., "Elastin is an Essential Determinant of Arterial Morphgenesis," Nature vol. 393, May, 1998, pp. 276–280.
Yi, Dean Y. et al., "Novel Arterial Pathology in Mice and Humans Hemizygous for Elastin," J. Clin. Invest., vol. 102, No. 10, Nov., 1998, pp. 1783–1787.
Urness, Lisa D., et al., "Arteriovenous Malformations in Mice Lacking Activin Receptor–Like Kinase–1," Nature Genetics, vol. 26, Nov., 2000, p. 1–4.
Weiss, Robert S., et al., "Inactivation of Mouse *HUS1* Results in Genomic Instability and Impaired Responses to Genotoxic Stress." Genes & Development, vol. 14, No. 15, p. 1886–1898.
Dean Y. Li et al.; Defective Angiogenesis In Mice Lacking Endoglin; Science, vol.284, May 28, 1999; pp. 1534–1537.

* cited by examiner

*Primary Examiner*—Scott D. Priebe
*Assistant Examiner*—Eleanor Sorbello
(74) *Attorney, Agent, or Firm*—Brinks Hofer Gilson & Lione

(57) ABSTRACT

Transgenic mice are genetically engineered for a deficiency in endoglin production. These mice may have a homozygous or hemizygous disruption of the endogenous endoglin gene. Homozygous mice exhibit a lack of endoglin production. The failure to produce endoglin results in arrested development of the vascular system of the mouse and no survival beyond E11.5. These mice and cells derived therefrom provide useful reagents for understanding the development and pathology of the mammalian vascular system.

8 Claims, 4 Drawing Sheets

(4 of 4 Drawing Sheet(s) Filed in Color)

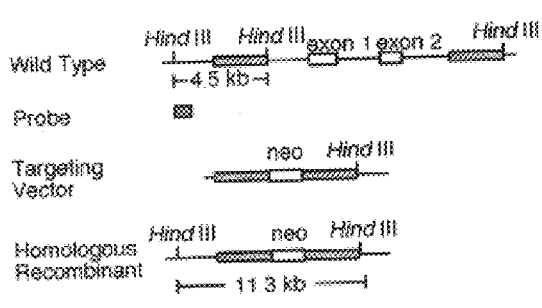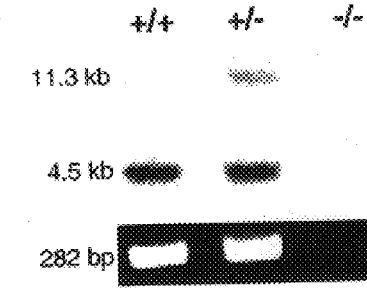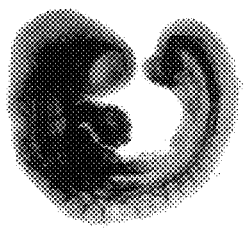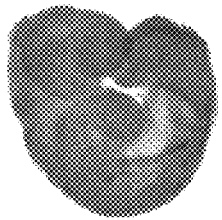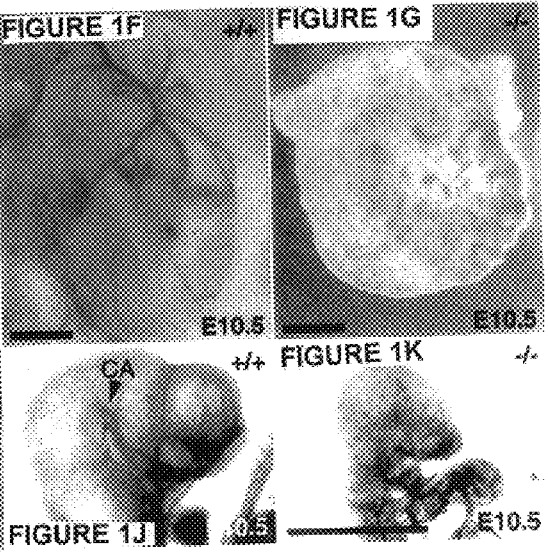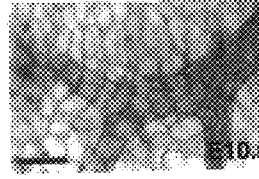

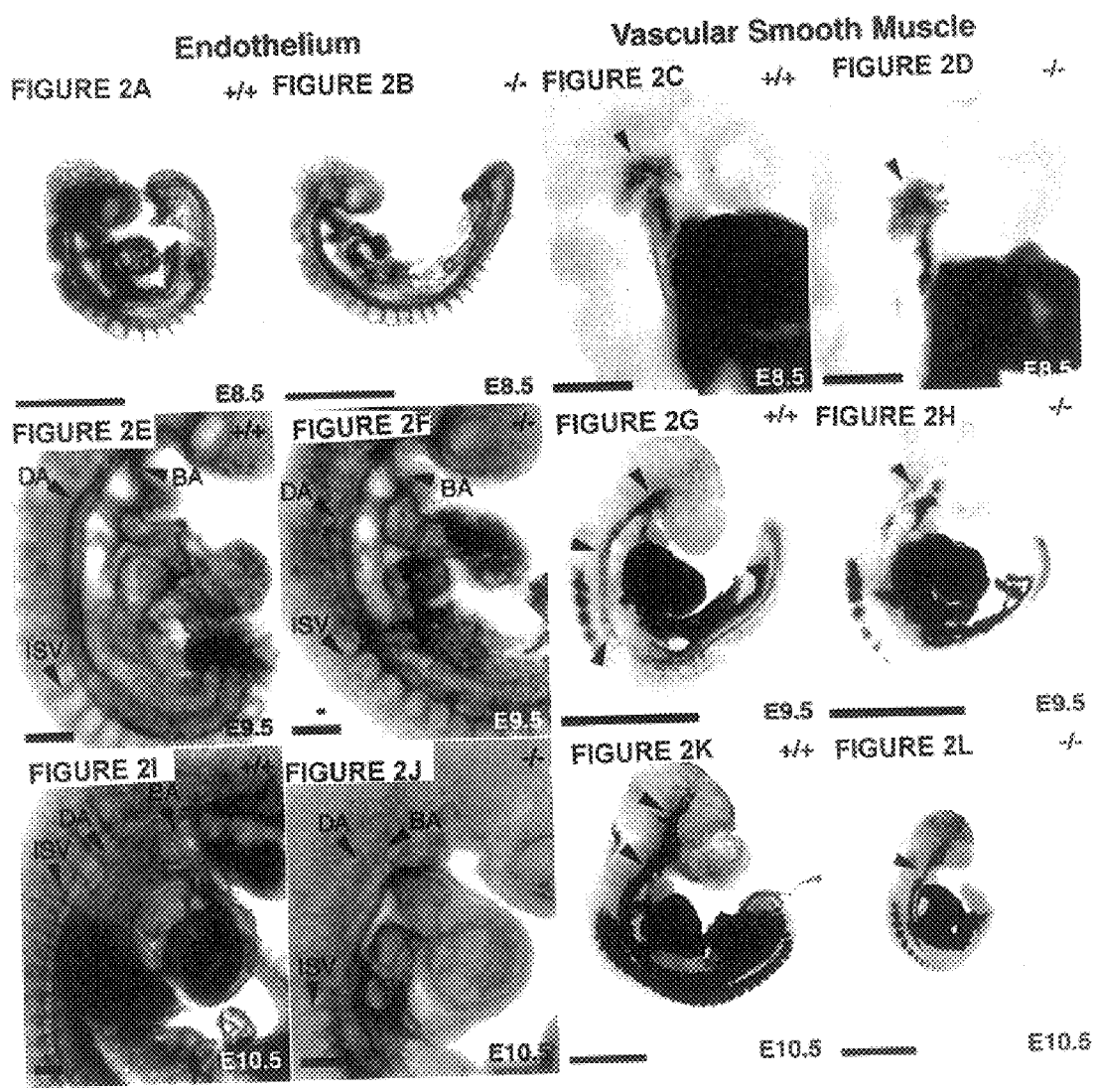

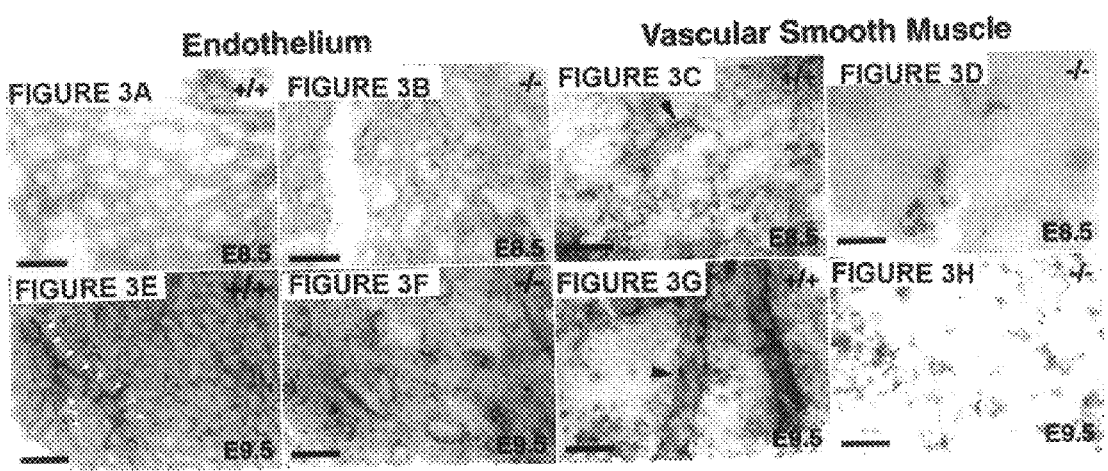

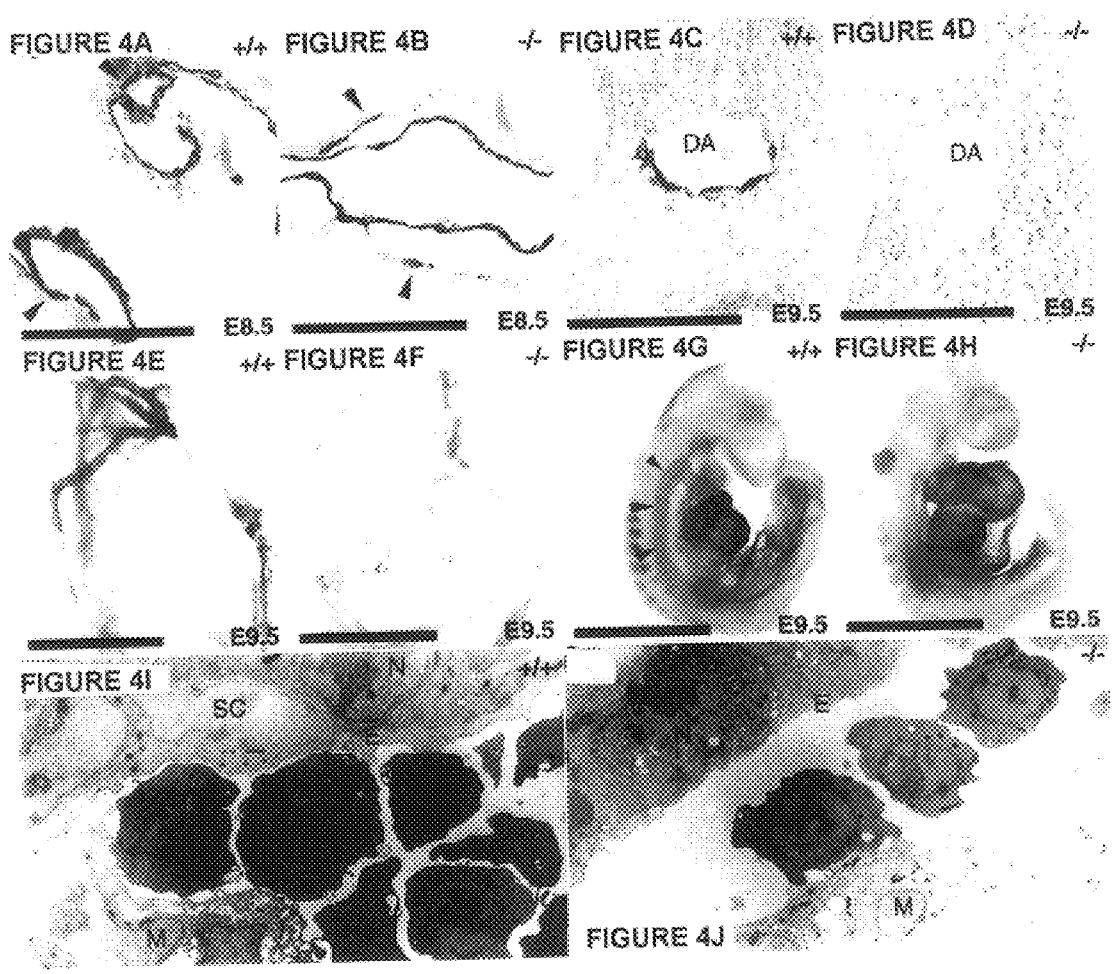

TRANSGENIC MOUSE WITH ENDOGENOUS ENDOGLIN GENE DISRUPTION

RELATED APPLICATIONS

This application is related to and claims the benefit of U.S. Provisional patent application Ser. No. 60/136,089 of Dean Li and Mark T. Keating, filed May 26, 1999 and entitled "Defective Angiogenesis in Mice Lacking Endoglin," which is incorporated herein by reference.

STATEMENT REGARDING FEDERALLY SPONSORED RESEARCH OR DEVELOPMENT

Work on this invention was sponsored in part by the National Institutes of Health Grant No. K08 HL03490-03. The Government may have certain rights in the invention.

BACKGROUND OF THE INVENTION

1. Field of the Invention

The present invention relates to transgenic mice for studying developmental biology and human disease. More specifically, the present invention relates to transgenic mice having a disrupted endogenous endoglin gene.

2. Technical Background

The use and study of laboratory animals has proven useful in understanding human disease. Animals can be kept in controlled conditions to observe disease pathology and to test new treatments for disease. However, animal models have limitations. Chief among these limitations is the large number of genetic differences between animals and humans. These differences sometimes reduce the usefulness of animal models in understanding and developing treatments for human disease. For example, some human diseases are caused by genetic factors that may not naturally occur in laboratory animals. For these and other reasons, transgenic animals have been developed.

A transgenic animal carries a genetic sequence (called a "transgene" or "heterologous sequence") that is not endogenous to that animal. The genetic sequence has been introduced into the germline of the animal or an ancestor of the animal at an early developmental stage.

For example, transgenic mice have been developed with an activated oncogene sequence. These mice are useful models in the study of cancer. Other transgenic animals have been developed which contain and express various genes for human proteins. Yet other transgenic animals have been made in which one or more genes have been mutated by either random or targeted insertion of a transgene or transgenes. These animals may serve as useful models for human diseases that are caused by genetic factors.

Even with a number of transgenic animals being developed, there is a need for animal models for a variety of human diseases. For example, the loss-of-function mutations in the human endoglin gene, ENG, cause hereditary hemorrhagic telangiectasia (HHT1), a disease characterized by vascular malformations. HHT is an autosomal dominant vascular dysplasia characterized by recurrent epistaxis, telangiectasia, gastrointestinal hemorrhage, and pulmonary, cerebral and hepatic arteriovenous malformations. McAllister et al., *Nature Genet.* 8:345 (1994); Guttmacher et al., *N. Engl. J. Med.* 33:918 (1995). Endoglin is a transforming growth factor beta (TGF-β) binding protein expressed on the surface of endothelial cells. ENG, the gene responsible for HHT1, encodes an endothelial transmembrane protein that binds to members of the TGF-β superfamily and their receptor complexes. St.-Jacques et al., *Endocrinology* 134:2645 (1994); J. R. Westphal et al., *J. Invest. Dermatol.* 100:27 (1993); H. Yamashita et al., *J. Biol. Chem.* 269:1995 (1994); Cheifetz et al., *J. Biol. Chem.* 267:19027 (1992); Barbara et al., *J. Biol. Chem.* 274:584 (1999). TGF-β signaling is required for the first stage of vascular development, vasculogenesis, in which the primary capillary network, comprised of interconnected and homogeneously sized endothelial tubes, is formed. Dickson et al., *Development* 121: 1845 (1995); Oshima, et al., *Dev. Biol.* 179: 297 (1996). The second stage of vascular development, angiogenesis, involves the remodeling of the primary endothelial network into a mature circulatory system. Folkman & D'Amore, *Cell* 87:1153 (1996); Yancopoulos et al., *Cell* 93:661 (1998); Flamme & Risau, *Development* 116:435 (1992); Pepper, *Cytokines and Growth Factor Rev.* 8:21 (1993); Kinglsey, *Genes Dev.* 8:133 (1994); Reddi, *Cytokine Growth Factor Rev* 8:11 (1997); Massague et al., *Trends Cell Biol.* 4:172 (1994).

The pathology of HHT1 is little understood. Moreover, since HHT1 results from a malformation of the vascular system, a model for HHT1 may result in greater understanding of other vascular related diseases and angiogenesis in tumors. Therefore, it would be an advancement in the art to provide an animal model for understanding the role of endoglin in vascular development. It would be a further advancement to provide cells from such animals for use in laboratory research.

Such animals and cells are disclosed herein.

BRIEF SUMMARY OF THE INVENTION

The invention provides transgenic mice in which the endogenous endoglin gene is disrupted. In certain embodiments, a transgenic mouse of the present invention is homozygous for endoglin gene disruption. A mouse which is homozygous for the endoglin gene disruption is designated "Eng−/−." As a result of the homozygous gene disruption, the mice are unable to produce endoglin, which is a transforming growth factor beta (TGF-β) binding protein expressed on the surface of endothelial cells. Due to this deficiency in endoglin, the development of the vascular system of the mice is arrested. Because of the arrested vascular system development, the Eng−/− mice do not live beyond embryonic (E) day 11.5. These mice are useful for understanding the development of the mammalian vascular system and suggest a pathogenic mechanism for hereditary hemorrhagic telangiectasia. These mice and cells derived from these mice may also be useful for the study of other angiogenesis-related phenomena such as obstructive vascular disease and tumor angiogenesis. These other phenomena are of considerable importance to public health.

A transgenic mouse of the present invention can be created by disrupting the endogenous endoglin gene (ENG). A targeting vector my be designed to replace the first two exons or other portion of ENG with a selectable marker gene sequence or other heterologous sequence by homologous recombination. A selectable marker gene sequence may comprise a gene conferring antibiotic resistance such as neomycin resistance. Other selectable markers are known in the art. In certain embodiments, a heterologous sequence other than a selectable marker is used to disrupt the ENG gene. Such sequences are introduced to destroy or alter the function of the ENG gene and include, for example, stop codons, portions of the ENG gene sequence that have been altered by mutations (including frameshift mutations, insertions, deletions, and point mutations), or sequences that code for portions of heterologous proteins. Insertions that disrupt the ENG gene by homologous recombination but do not employ a selectable marker may nevertheless be detected by screening methods; for example, polymerase chain reaction (PCR) based strategies may be used to screen large numbers of transfected embryonic stem (ES) cells for the desired insertion.

Targeted ES cells are identified and used to generate chimeric mice by morula aggregation. Well-known techniques, such as Southern analysis or PCR, may be used to confirm germline transmission of the targeted allele.

The present invention also provides cells derived from transgenic Eng−/− mice and mouse embryos. A variety of methods for isolating and culturing such cells are known to those of skill in the art. In certain embodiments, a cell is derived from a transgenic mouse embryo homozygous for endogenous endoglin disruption, said disruption resulting from insertion of a selectable marker gene sequence or other heterologous sequence into the genome by homologous recombination, wherein the disruption results in a lack of expression of the endoglin gene product, and wherein the lack of expression of the endoglin gene product results in arrested development of the vascular system of the mouse embryo. In other embodiments of the present invention, the cell derived from a transgenic Eng−/− mouse or embryo is an embryonic stem cell.

A transgenic Eng−/− mouse is deficient in development of the vascular system and does not live past E11.5. Therefore, it may prove advantageous to provide a transgenic mouse hemizygous for disruption of an endogenous endoglin gene, designated as Eng+/−. A transgenic Eng+/− mouse may be created by the disruption of one copy of the endogenous endoglin gene as discussed above. The disruption may result from the insertion of a selectable marker gene sequence or other heterologous sequence into the genome by homologous recombination. A selectable maker make include a gene sequence conferring resistence to an antibiotic such as neomycin.

The present invention also provides cells derived from an Eng+/− mouse or embryo and mouse cells that are hemizygous for disruption of the endogenous endoglin gene. In other embodiments of the present invention, the cell derived from a transgenic Eng+/− mouse is an embryonic stem cell.

These and other features and advantages of the present invention will become more fully apparent from the Detailed Description.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

A more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 1 illustrates the targeted inactivation of murine Eng and the role of endoglin in defective vascular development; FIG. 1A is a depiction of restriction maps of an Eng genomic fragment, targeting construct, and predicted structure of targeted Eng allele; FIG. 1B is a reproduction of Southern analysis of yolk sac DNA from E10.5 embryos probed for homologous recombination; FIG. 1C is a reproduction of Northern analysis showing the absence of Eng transcript in E9.5 Eng−/− mice; FIGS. 1D and 1E show a color reproduction of endoglin immunostain of E10.5 embryos demonstrating the presence and absence of endoglin, respectively, in Eng+/+ and Eng−/− mice; FIGS. 1F and 1G are photomicrographs of E10.5 yolk sac; FIGS. 1H and 1I are PECAM immunostains of yolk sacs at E10.5; and FIGS. 1J and 1K are PECAM immunostains of head vessels at E10.5.

FIG. 2 illustrates that poor vascular smooth muscle development in Eng−/− embryos precedes disruption in endothelial remodeling (scale bars represent 1.0 mm, except in FIGS. 2C, 2D, 2E, 2F, 2I, and 2J, in which the scale bars represent 0.2 mm); FIGS. 2A and 2B are photographs of mouse embryos at E8.5; FIGS. 2C and 2D show the cranial most aspect of the dorsal aortae (arrowheads) at E8.5; FIGS. 2E and 2F are photographs of mouse embryos at E9.5; FIGS. 2G and 2H are photographs of mice embryos showing the progression of vsmc formation in the Eng+/+ and Eng−/− embryos; FIGS. 2I and 2J are photographs of mouse embryos showing that there is a marked maturation of endothelial organization in Eng+/+ embryos that is lacking in Eng−/− embryos; and FIGS. 2K and 2L are photographs of mouse embryos showing that vsmcs surround the carotid arteries and the dorsal aortae in Eng+/+ embryos (arrowheads). In comparison, vsmc formation in Eng−/− embryos remains incomplete and sparse.

FIG. 3 illustrates that poor vascular smooth muscle development in Eng−/− yolk sacs precedes disruption in endothelial remodeling (scale bars represent 0.1 mm); FIGS. 3A and 3B are photographs of immunohistochemical assays using antisera to endothelial markers Flk-1 performed at E8.5; FIGS. 3C and 3D are photographs of immunohistochemical assays using the vsmc marker α-smc actin at E8.5; FIGS. 3E and 3F are photographs of immunohistochernical assays using PECAM.; and FIGS. 3G and 3H are photographs of immunohistochemical assays using the vsmc marker α-smc actin.

FIG. 4 illustrates the poor vsmc formation in Eng−/− mice (scale bars represent 0.1 mm for FIGS. 4A, 4B, 4C, and 4D and 1.0 mm for panels 4E, 4F, 4G, and 4H); FIGS. 4A, 4B, 4C, and 4D are photographs of transverse sections of α-smc actin-stained embryos and yolk sacs at E9.5; FIGS. 4E, 4F, 4G, and 4H are photographs of in situ hybridization of yolk sacs and embryos at E9.5 using a riboprobe for the vsmc marker, SM22α; FIGS. 4I and 4J are photographs of electron micrograph analysis of Eng+/+ and −/− yolk sac at E9.5.

DETAILED DESCRIPTION OF THE INVENTION

The present invention is directed to novel transgenic animals. In certain embodiments of the invention, the transgenic animal is a mouse wherein an endogenous gene encoding endoglin (ENG) has been disrupted by homologous recombination with a targeting vector. Mice lacking endoglin die by gestational day 11.5 from defective vascular development. Loss of endoglin causes poor vascular smooth muscle development and arrested endothelial remodeling. These results demonstrate that endoglin is essential for angiogenesis and suggest a pathogenic mechanism for HHT1.

A transgenic mouse of the present invention may be created by the targeted inactivation of murine Eng. FIG. 1A depicts restriction maps of a mouse Eng genomic fragment, targeting construct, and predicted structure of a successfully targeted Eng allele. The hatched boxes represent regions of homology shared by the targeting vector and genomic Eng. The probe for Southern analysis detects an 11.3 kb Hind III fragment from the disrupted allele and a 4.5 kb Hind III fragment from the wild type allele.

Consistent with the present invention, a targeting vector was designed to replace the first two exons of ENG with a gene segment conferring neomycin resistance. The targeting vector was made by using 3.5 kb and 5.2 kb fragments from a murine genomic ES BAC clone, respectively, for the 5' and 3' regions of homology. Culture, selection and screening of targeted clones were as described in D. Y. Li et al., Nature 393:276 (1998). Three targeted embryonic stem cell clones were identified and used to generate chimeric mice by morula aggregation. There was no evidence of random integration in the homologous recombinant clones used for chimera generation. Resulting chimeric animals were crossed to C57B1/6J mice and germline transmission was confirmed. Genotypes were assigned on the basis of Southern analysis of DNA extracted from tails, embryos, or yolk sacs.

Referring to FIG. 1B, Southern analysis at E10.5 confirmed germline transmission of the targeted allele. Referring to in FIG. 1C, RNA analysis was performed to confirm the absence of Eng transcripts in E9.5 Eng−/−mice. Primers amplifying a 427 bp region of Eng were used to amplify cDNA from total RNA.

Referring now to FIGS. 1D, and 1E, immunohistochemistry detected endoglin in the endothelium of Eng+/+ and Eng+/− mice by E8.5, but neither endoglin protein nor MRNA was detected in Eng−/− mice.

The life expectancy, fertility, and gross appearance of Eng+/− F1 and F2 mice were normal; however, no homozygotes were found among 150 newborn animals from heterozygous intercrosses. By examining embryos from heterozygous intercrosses at different developmental stages, it was determined that no Eng−/− mice survive after E11.5.

Referring to FIGS. 1F and 1G, the yolk sacs of E10.5 mice were analyzed by photomicrographs. The vasculature of the Eng+/+ yolk sac is well defined. Pockets of red blood cells are observed in Eng−/− yolk sac with no discernible vessels. However, as shown in the PECAM immunostains of yolk sacs at E10.5 of FIGS. 1H and 1I, Eng−/− endothelium fails to organize into vitelline vessels.

At E10.5 the head vessels were analyzed by PECAM immunostains as shown in FIGS. 1J and 1K. The perineural capillary plexus fails to organize and the carotid artery (CA) is atretic in Eng−/− embryos.

Referring now to FIG. 2, poor vascular smooth muscle ("vsmc") development in Eng−/− embryos precedes disruption in endothelial remodeling. As shown in the photographs of FIGS. 2A and 2B the organization of Eng+/+ and Eng−/− endothelial tubes is indistinguishable at E8.5. As seen in FIGS. 2C and 2D, the initiation of vsmc differentiation occurs at the cranial-most aspect of the dorsal aortae (arrowheads) at E8.5. Referring to FIGS. 2E and 2F where the dorsal aorta (DA), branchial arches (BA), and intersomitic vessels (ISV) are identified, the endothelial organization of Eng+/+ and Eng−/− embryos remains similar at E9.5.

FIGS. 2G and 2H illustrate that, after the initiation of vsmc differentiation, vsmc formation in the Eng+/+ embryos extends caudally in the dorsal aortae and rostrally to the carotid arteries (arrowheads). However, vsmc development in Eng−/− embryos fails to progress from E8.5 to E9.5.

Referring to FIGS. 2I and 2J, there is a marked maturation of endothelial organization in Eng+/+ embryos that is lacking in Eng−/− embryos. Large arteries like the carotid arteries, dorsal aortae, and intersomitic vessels are atretic in Eng−/− embryos. In FIGS. 2K and 2L, vsmcs surround the carotid arteries and the dorsal aortae in Eng+/+ embryos (arrowheads). In comparison, vsmc formation in Eng−/− embryos remains incomplete and sparse.

Referring now to FIG. 3, poor vascular smooth muscle development in Eng−/− yolk sacs precedes disruption in endothelial remodeling. Immunohistochemistry was employed using antisera to endothelial markers Flk-1 and PECAM. An imnmunohistochemical assay using antiseral to endothelial markers Flk-1 was performed at E8.5. As shown in FIGS. 3A and 3B a primary endothelial network is present in both Eng +/+ and Eng−/− yolk sacs.

An immunohistochemical assay using the vsmc marker α-smc actin was performed on embryos at E8.5. Referring to FIGS. 3C and 3D, vsmcs (arrowhead) developed around selective endothelial tubes from Eng+/+ yolk sacs. However, vsmc formation is scarce and unorganized in Eng−/− yolk sacs.

An immunohistochemical assay using PECAM was performed at E9.5. As seen in FIGS. 3E and 3F, the primary endothelial network remodels into distinct vessels in Eng+/+ yolk sacs (arrowheads). There is no evidence of endothelial remodeling in E9.5 Eng−/− yolk sacs.

An additional immunohistochemical assay using the vsmc marker α-smc actin was performed at E9.5. Referring to FIGS. 3G and 3H, vsmcs define distinct vessels in Eng+/+ yolk sac but not in Eng−/− yolk sac (arrowheads).

Referring to FIGS. 4A, 4B, 4C, and 4D, transverse sections of α-smc actin stained embryos and yolk sacs were photographed at E9.5. As seen in FIGS. 4A and 4B, vsmcs can be identified between the endoderm and endothelium in Eng+/+ and are scarce in Eng −/− yolk sacs (arrowheads). Cross reactivity of α-smc actin antisera with the mesothelium is observed in both Eng+/+ and Eng−/− yolk sacs Referring to FIGS. 4C and 4D, vsmcs form around the dorsal aortae of Eng+/+ embryos. No vsmcs are identified in the dorsal aortae of Eng−/− embryos.

Referring to FIGS. 4E, 4F, 4G, and 4H, yolk sacs and embryos at E9.5 were hybridized in situ using a riboprobe for the vsmc marker, SM22α. As seen in FIGS. 4E and 4F, expression of SM22α outlines Eng+/+ vessels (arrowheads) but is absent in Eng−/− yolk sacs. Moreover, FIGS. 4G and 4H show that expression of SM22α is present throughout the dorsal aortae of Eng+/+ embryos (arrowheads), but is absent from Eng−/− embryos.

Referring to FIGS. 4I and 4J, electron micrograph analysis of Eng+/+ and−/− yolk sacs was performed at E9.5. Supporting cells (SC), presumably vsmc or pericytes, are seen between the endoderm (N) and endothelium (E) of Eng+/+ yolk sacs, but are absent in Eng −/− yolk sac. The mesothelium is identified (M).

All publications, patents, and patent applications cited herein are hereby incorporated by reference.

EXAMPLES

The following examples are given to illustrate various embodiments which have been made within the scope of the present invention. It is to be understood that the following examples are neither comprehensive nor exhaustive of the many types of embodiments which can be prepared in accordance with the present invention.

Example 1

Eng−/− Mice Embryos Exhibit an Absence of Vascular Organization.

At E10.5, Eng−/− mice were three times smaller than Eng+/+ mice and had fewer somites (18–22 in Eng−/− mice vs. 32–35 in Eng+/+ mice), FIGS. 1D and 1E. As can be seen in FIGS. 1F and 1G, the Eng−/− embryos exhibited an absence of vascular organization and the presence of multiple pockets of red blood cells on the yolk sac surface. Expression of endothelial markers such as Flk-1, Flt-1, Tie-1, and Tie-2 and hematopoietic markers Gata-1 and I1-3r were not disrupted in Eng−/− mice. Reverse transcriptase/polymerase chain reactions for these molecular markers were performed as previously described Shalaby et al., *Nature* 376: 62 (1995). Thus, in contrast to TGF-β1 or its signaling receptor, there is no evidence that endoglin is required for vasculogenesis. Dickson, et al., *Development* 121: 1845 (1995); Oshima, et al., *Dev. Biol.* 179: 297 (1996). Absence of organized vessels in the Eng−/− yolk sacs was confirmed by immunohistochemical staining for the endothelial marker, platelet-endothelial cell adhesion molecule (PECAM), the results of which are shown in FIGS. 1H and 1I. Immunoperoxidase staining of mouse embryos was performed using monoclonal antibodies to PECAM (Pharmingen, San Diego, Calif.), endoglin (Pharmingen), FLK-1 (Santa Cruz Biotechnology, Santa Cruz, Calif.) or α smc actin (clone 1A4, 1:500; Sigma, St. Louis, Mo.). Staining was developed in 3,3'-diamin -benzidine chromagen (Vector Laboratories, Bulingame, Calif.). Sections of stained tissue were counterstained with Eosin B. The persistence of an immature perineural vascular plexus indicated a failure of endothelial remodeling in Eng−/− embryos (FIG. 1, J and K). At E10.5, the cardiac tube did not complete rotation in Eng−/− mice and was associated with a serosanguinous pericardial effusion. Although the cardiac tube continued to circulate blood at E10.5, by E11.5 there was evidence of resorption and necrosis in Eng−/− embryos.

Example 2

Absence of Endoglin Affects the Development of the Vascular System.

PECAM immunostains demonstrated that the first organ system affected in Eng−/− embryos was the vascular system. As can be seen in FIGS. 2A, 2B, 2E, and 2F, the endothelial organization of Eng+/+ and Eng−/− embryos was similar at E8.5 and E9.5. However, between E9.5 and E10.5, vascular development was disrupted in Eng−/− mice. While there was extensive endothelial remodeling of the vasculature with expansion of existing vessels and sprouting and branching of new ones in Eng+/+ embryos at E10.5, the major vessels including the dorsal aortae, intersomitic vessels, branchial arches, and carotid arteries were atretic and disorganized in Eng−/− embryos as seen in FIGS. 1J, 1K, 2I, and 2J.

Example 3

Disrupted Angiogenesis is due to Poor VMSC Development

Because TGF-β signaling has been shown to regulate vsmc differentiation in vitro, we hypothesized that the disrupted angiogenesis in Eng−/− embryos was due to poor vsmc development. Pepper, *Cytokines and Growth Factor Rev.* 8:21(1993); Kinglsey, *Genes Dev.* 8:133 (1994); Reddi, *Cytokine Growth Factor Rev* 8:11 (1997); Massague, et al., *Trends Cell Biol.* 4: 172 (1994). Embryos were stained with an α smooth muscle cell actin (α-smc actin) antibody to assess vsmc development. At E8.5 (10–12 somites stage), Eng+/+ and Eng−/− embryos were indistinguishable with a foci of vsmcs forming at the cranial-most aspect of the dorsal aortae (FIG. 2, C and D). By E9.5 (18–20 somites stage), Eng+/+ vsmcs had extended rostrally to the carotid arteries and caudally through the dorsal aortae (FIG. 2G). At E10.5, vsmcs of the Eng+/+ embryos surrounded the dorsal aortae, branchial arches, and carotid arteries as shown in FIG. 2K. In contrast, there was poor vsmc formation of Eng−/− embryos at both E9.5 and E10.5, illustrated in FIGS. 2H and 2L. Thus, significant differences is Eng+/+ and Eng−/− vsmc development were apparent by E9.5 and preceded the differences in endothelial organization observed between E9.5 and E10.5.

Example 4

VSMC Defect Precedes Defect in Endothelial Remodeling.

The failure in endothelial remodeling was not restricted to embryonic tissue. Vascular organization of E8.5 Eng+/+ and Eng−/− yolk sacs was similar and consisted of a primary endothelial network (FIGS. 3A and 3B). At E9.5, distinct vessels were forming in Eng+/+ yolk sac as shown in FIG. 3E. In contrast, the vasculature of E9.5 Eng−/− yolk sacs failed to organized (FIG. 3F). By E10.5, distinct vessels were prominent in Eng+/+ mice but absent in Eng−/− mice (FIGS. 1H and 1I). Though disruption of endothelial organization occurs between E9.5 and E10.5, poor vsmc development is evident by E8.5 in Eng−/− yolk sacs. At E8.5, vsmcs coated selective endothelial tubes in the Eng+/+ yolk sac but were scarce in Eng−/− yolk sac (FIG. 3C and 3D). By E9.5, vsmcs in Eng+/+ yolk sacs outlined distinct vessels whereas no progression was seen in Eng−/− yolk sacs (FIGS. 3G and 3H). Thus, the vsmc defect in Eng−/− extraembryonic tissue was evident by E8.5 and preceded the defect in endothelial remodeling.

Example 5

Endoglin Is Required for Normal VSMC Development.

Histologic analysis, in situ hybridization, and ultrastructural analysis were used to confirm that vascular development is disrupted in Eng−/− mice. Cross sections of α-smc actin immunostains identified vsmcs between the endoderm and endothelium of the yolk sac. As illustrated in FIGS. 4 A and 4B, few vsmcs formed between these layers in Eng−/− compared to Eng+/+ yolk sacs. Transverse sections of dorsal aortae showed vsmc developing around the endothelium of an Eng+/+ embryo at E9.5 (FIG. 4C). No vsmcs are observed in a comparable section of an Eng−/− embryos (FIG. 4D). In situ hybridization for an early molecular marker of vsmc development, SM22α, showed a failure of vsmc to develop in E9.5 Eng−/− yolk sac and embryos. Hybridization was performed at 70° C. using a riboprobe previously described by Li, et al., *Circ.* 78:188 (1996). Sense riboprobes showed no hybridization (FIGS. 4, E, F, G, and H). Electron micrographs of E9.5 Eng−/− yolk sacs illustrated the absence of supporting cells, presumably pericytes or vsmc precursors, around the endothelium of the capillary network. Tissue was fixed in 3% glutaraldehyde and sequentially stained with osmium tetroxide, tannic acid and uranyl acetate. After dehydration, tissue was embedded in Epon. Thin sections (60 nm) were counterstained with uranyl acetate and lead citrate and examined on a Jeol 1200 electron microscope (FIGS. 4I and 4J). These data support the conclusion that endoglin is required for normal vsmc development.

Angiogenesis involves the differential growth and sprouting of endothelial tubes, and recruitment and differentiation of mesenchymal cells into vsmcs and pericytes. Folkman & D'Amore, *Cell* 87:1153 (1996); Yancopoulos et al., *Cell* 93 661 (1998); Flamme & Risau, *Development* 116:435 (1992). The experiments described herein demonstrate that endoglin is required for both processes. Because endoglin binds members of the TGF-β superfamily and interacts with their receptors, it is likely that endoglin regulates TGF-β signaling. This conclusion is supported by in vitro heterotypic co-culture experiments demonstrating that endothelial cells induce vascular smooth muscle differentiation through a TGF-β pathway. Hirschi et al., *J. Cell. Bio.* 141:805 (1998). Thus, our experiments indicate that TGF-β signaling is essential for angiogenesis.

Communication between the endothelium and mesenchyme is important for angiogenesis. Folkman & D'Amore, *Cell* 87:1153 (1996); Yancopoulos et al., *Cell* 93: 661 (1998); Flamme & Risau, *Development* 116:435 (1992). Mesenchymal cells signal endothelial cells via the angiopoietin/Tie-2 signaling pathway, while endothelial cells induce differentiation of pericytes through the platelet-derived growth factor (PDGF) signaling pathway. C. Suri et al., *Cell* 87:1171 (1996); T. Sato et al., *Nature* 376:7074 (1995); Maisonpierre et al., *Science* 277:55 (1997); Lindahl et al., *Science* 277:242 (1997); Soriano, *Genes Dev.* 8:1888 (1994). While PDGF signaling is important for microvascular pericyte formation in the brain, our data demonstrate that endothelial expression of endoglin is essential for vsmc development throughout the circulatory system. The subsequent failure of the endothelium to remodel in Eng−/− mice following arrested vsmc development suggest that vsmcs may also play a role in regulating endothelial organization. Without being bound by any particular theory, it appears that endoglin mediates a third pathway of endothelial-mesenchymal communication that is essential for angiogenesis and important to the pathogenesis of vascular disease.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

We claim:

1. A transgenic mouse embryo homozygous for endogenous endoglin gene disruption, wherein the disruption results in arrested development of the vascular system of the mouse.

2. The transgenic mouse embryo of claim 1, wherein the disruption results in a lack of expression of the endoglin gene product.

3. The transgenic mouse embryo of claim 1, wherein the disruption results from insertion of a selectable marker gene sequence or other heterologous sequence into the genome by homologous recombination.

4. The transgenic mouse embryo of claim 3, wherein the selectable marker gene sequence comprises a gene conferring neomycin resistance.

5. The transgenic mouse embryo of claim 3, wherein the disruption results in a lack of expression of the endoglin gene product.

6. A cell derived from the mouse embryo of claim 1.

7. A cell derived from the mouse embro of claim 3.

8. A cell derived from a transgenic mouse embryo homozygous for endogenous endoglin gene disruption, said disruption resulting from insertion of a selectable marker gene sequence or other heterologous sequence into the genome by homologous recombination, wherein the disruption results in a lack of expression of the endoglin gene product, and wherein the lack of expression of the endoglin gene product results in arrested development of the vascular system of the mouse embryo.

* * * * *